US012133838B2

(12) United States Patent
Bellini et al.

(10) Patent No.: US 12,133,838 B2
(45) Date of Patent: Nov. 5, 2024

(54) HOMOTAURINE-ENRICHED COMPOSITIONS AND METHODS OF USE FOR ANIMAL HEALTH

(71) Applicant: FB Maria srl, Ascoli Piceno (IT)

(72) Inventors: Francesco Bellini, Calgary (CA); Lise Hebert, Montreal (CA); Andrea Spaterna, Matelica (IT); Marco Marchetti, San Benedetto del Tronto (IT)

(73) Assignee: FB Maria srl, Ascoli Piceno (IT)

( * ) Notice: Subject to any disclaimer, the term of this patent is extended or adjusted under 35 U.S.C. 154(b) by 290 days.

(21) Appl. No.: 17/558,652

(22) Filed: Dec. 22, 2021

(65) Prior Publication Data

US 2022/0184005 A1 Jun. 16, 2022

Related U.S. Application Data

(63) Continuation of application No. 15/777,383, filed as application No. PCT/CA2016/051354 on Nov. 18, 2016, now Pat. No. 11,224,579.

(30) Foreign Application Priority Data

Nov. 18, 2015 (CA) .................... 2912611

(51) Int. Cl.
*A61K 31/16* (2006.01)
*A61K 9/00* (2006.01)
*A61K 31/145* (2006.01)
*A61P 25/28* (2006.01)

(52) U.S. Cl.
CPC .......... *A61K 31/145* (2013.01); *A61K 9/0056* (2013.01); *A61P 25/28* (2018.01)

(58) Field of Classification Search
CPC ..................................... A61K 31/16
USPC ....................................... 514/578
See application file for complete search history.

(56) References Cited

FOREIGN PATENT DOCUMENTS

| EP | 3219306 A1 | 9/2017 |
|----|------------|--------|
| WO | 2010/096925 A1 | 9/2010 |
| WO | 2011/031304 A2 | 3/2011 |

OTHER PUBLICATIONS

Berge et al., "Pharmaceutical Salts", Journal of Pharmaceutical Sciences, vol. 66 (1), 1-19 (1977).
Dimakopoulos et al., "Aspects of Neurodegeneration in the Canine Brain", The Journal of Nutrition, vol. 132, Issue 6, Jun. 2002, pp. 1579S-1582S.
Gervais et al., "Targeting soluble Aβ peptide with Tramiprosate for the Treatment of brain amyloidosis", Neurobiology of Aging 28 (2007) pp. 537-547.
Martorana et al., "Homotaurine induces measurable changes of short latency afferent inhibitions in a group of mild cognitive impairment individuals", Frontiers in Aging Neuroscience, vol. 6, Article 254, pp. 1-7, Sep. 2014.
Mongillo et al., "Spatial reversal training is impaired by aging in pet dog", Age, 2013, 35(6), 2273-2282.
Shuangchan et al., "Tramiprosate protects neurons against ischemic stroke by disrupting the interaction between PSD95 and nNOS", Neuropharmacology, vol. 83, Apr. 24, 2014, pp. 107-117.
Aisen et al., Tramiprosate in mild-to-moderate Alzheimer's disease—a randomized, double-blind, placebo-controlled, multi-center study (the Alphase study), Arch Med Sci 2011; 7, 1:102-111.
Cavanaugh et al., "Animal Models of Alzheimer Disease: Historical Pitfalls and a Path Forward", ALTEX, 2014; 31(3): 279-302.
Chishti et al., "Early-onset Amyloid Deposition and Cognitive Deficits in Transgenic Mice Expressing a Double Mutant Form of Amyloid Precursor Protein 695", The Journal of Biological Chemistry, vol. 276, No. 24, Issue of Jun. 15, pp. 21562-21570, 2001.
Davis et al., "Prevention approaches in a preclinical canine model of Alzheimer's disease: benefits and challenges", Frontiers in Pharmacology, Mar. 2014, vol. 5, Article 47, pp. 1-14.
Denenberg et al., "Therapeutic options for treatment of cognitive dysfunction syndrome in companion animals", Journal of Veterinary Behavior, vol. 5, No. 3, May/Jun. 2010.
Dodart et al., "Immunization reverses memory deficits without reducing brain AB burden in Alzheimer's disease model", Nature neuroscience, vol. 5, No. 5, May 2002, pp. 452-457.
Head et al., "A Two-Year Study with Fibrillar B-Amyloid (AB) Immunization in Aged Canines: Effects on Cognitive Function and Brain AB", The Journal of Neuroscience, Apr. 2, 2008, 28(14): 3555-3566.
Janus et al., "Aβ peptide immunization reduces behavioural impairment and plaques in a model of Alzheimer's disease", Nature, vol. 408, 21/Dec. 28, 2000, pp. 979-982.
Landsberg, "Therapeutic agents for the treatment of cognitive dysfunction syndrome in senior dogs", Progress in Neuro-Psychopharmacology & Biological Psychiatry, 29 (2005), pp. 471-479.
Laurijssens et al., "Animal models of Alzheimer's disease and drug development", Drug Discovery Today: Technologies| Translational pharmacology, vol. 10, No. 3, 2013, pp. e319-e327.

(Continued)

*Primary Examiner* — Raymond J Henley, III
(74) *Attorney, Agent, or Firm* — BCF LLP

(57) ABSTRACT

The present disclosure generally relates to compounds comprising homotaurine that may be used in improving the general mental condition and/or general brain function of a non-human animal, and for the prophylaxis of chronic, aging-related mental deterioration in non-human animals. In addition, the present disclosure generally relates to compositions comprising homotaurine that may be used in determining whether a candidate veterinary compound and/or a candidate formulation can improve general mental condition and/or general brain function of animals and for the prophylaxis of chronic, aging-related mental deterioration in non-human animals.

18 Claims, 1 Drawing Sheet

(56) References Cited

OTHER PUBLICATIONS

Sasaguri et al., "APP mouse models for Alzheimer's disease preclinical studies", The EMBO Journal, vol. 36, No. 17, 2017, pp. 2473-2487.

Sarasa et al., "Natural Non-Transgenic Animal Models for Research in Alzheimer's Disease", Current Alzheimer Research, 2009, vol. 6, No. 2, pp. 171-178.

Savonenko et al. "Alzheimer's Therapeutics: Translation of Preclinical Science to Clincal Drug Development", Neuropsychopharmacology Reviews (2012) 37, pp. 261-277.

Schenk et al., "Immunization with amyloid-β attenuates Alzheimer-disease-like pathology in the PDAPP mouse", Nature, vol. 400, Jul. 8, 1999, pp. 173-177.

Van Dam et al., "Animal models in the drug discovery pipeline for Alzheimer's disease", British Journal of Pharmacology, (2011), 164, pp. 1285-1300.

Youssef et al., "Pathology of the Aging Brain in Domestic and Laboratory Animals, and Animal Models of Human Neurodegenerative Diseases", Veterinary Pathology (2016), vol. 53(2), pp. 327-348.

HOMOTAURINE-ENRICHED COMPOSITIONS AND METHODS OF USE FOR ANIMAL HEALTH

CROSS-REFERENCE TO RELATED APPLICATIONS

This application is a Continuation application of U.S. patent application Ser. No. 15/777,383, filed on May 18, 2018, which claims priority to and benefit from Canadian Patent Application CA 2,912,611, filed on Nov. 18, 2015, the disclosures of which are incorporated herein by reference in their entireties.

FIELD OF TECHNOLOGY

The present disclosure generally relates to compositions that may be used in improving the general mental condition and/or general brain function of a non-human animal, and for the prophylaxis of chronic, aging-related mental deterioration in non-human animals. In addition, the present disclosure generally relates to compositions that may be used in determining whether a candidate veterinary compound and/or a candidate formulation can improve general mental condition and/or general brain function of non-human animals and for the prophylaxis of chronic, aging-related mental deterioration in non-human animals.

BACKGROUND INFORMATION

Animals play an important role in many people's lives. In addition to seeing-eye dogs and dogs that can be trained to detect seizures, animals can also be used in occupational therapy, speech therapy, or physical rehabilitation to help patients recover. Aside from these designated therapeutic roles, animals are also valued as companions, which can affect the quality of human lives. The pet industry in the United States and many other countries is booming. Americans, for example, own more pets than ever before. Growth in the sector is derived both from increasing pet ownership as well as from increased spending per pet. Pet pampering is becoming the norm, as pet owner spending has moved far beyond simple food and grooming expenses to include innovative and specialized premium products and medical treatments. People increasingly view their pets as part of the family and are willing to spend even during difficult economic times. According to the American Pet Product Association (APPA), Americans spent approximately $47.7 billion on pet products and services in 2010, an increase of 4.8% over 2009. Since 1988, pet ownership has expanded from 56% of households to 62%.

Like people, animals (non-human animals) suffer from diseases and require proper care from the veterinarians, the farmers and the pet owners. Keeping animals healthy and treating them with dignity is one of the main objectives of the animal health industry and applies equally to companion animals, livestock and wild animals.

Aging has long been associated with a gradual decline in memory, cognition and thinking abilities. Previously, the deterioration of memory, cognition and thinking abilities has been considered as a normal, unmodifiable process as a result of aging. Research as shown however, that this progression can be delayed and/or slowed, by improving the overall protection of brain cells during the normal course of aging.

Aging and a gradual decline in memory and cognitive functions is not a malady that is specific to humans only; it is also observed in non-human animals, for example in companion animals such as in canines (e.g., dogs) and felines (e.g., cats), and may occur in other non-human animal species. For example, Cognitive Dysfunction Syndrome (CDS) represents a group of symptoms related to the aging of the canine and feline brain. Although the initial symptoms of CDS are mild, the symptoms gradually worsen over time and are generally referred to as "cognitive decline". In some canine breeds, and moreover in breeds of large dogs, the onset and rapid progression of CDS is a well-known phenomenon and often results in near to complete incapacitation of the affected animal.

Similar in its symptomology to Alzheimer's disease in humans, canine/feline cognitive dysfunction may be caused by physical and chemical changes in the brain that result in a progressive decline and loss of mental cognition in the affected animal. Studies have shown that some older dogs with cognitive dysfunction have brain lesions similar to those that physicians see in Alzheimer's human patients. The result of these changes may be manifested by one or more of a number of CDS symptoms such as aging-related behavioral changes in canines, and also in felines, including: frequent incidents of soiling while indoors or in areas other than where the animal has been trained and has perpetually utilized for such a purpose (e.g. the location of a litterbox for a cat); a loss of stamina or chronic fatigue; it exhibits a lack of familiarity with places either indoors or outdoors even though the animal has been familiar with the location throughout its life; unfocused wandering and staring at walls or into space and becoming "trapped" behind familiar furniture or in room corners; the animal trouble finding and using doors and negotiating stairways despite having no apparent deterioration of its muscular co-ordination or eyesight; the animal, although undistracted, does not respond to her/his name or familiar voices and voice commands; the animal is withdrawn and unwilling to play or otherwise interact (unlike what may be described as a generally aloof behaviour in some felines); it is reluctant or refuses to go for walks (e.g., a canine) or to even go outside despite never hesitating to do so in its younger years; it does not recognize or is startled by family members, toys, or other cues that it has been familiar with and exposed to on a constant basis throughout its life; it frequently trembles or shakes uncontrollably (despite not being exposed to a cold temperature or being unstartled) either while standing or lying down; it paces or wanders aimlessly throughout the house as if it is unfamiliar with its location or environment; it has difficulty learning new tasks, commands, or routes; for canines, sleeping more during the day and less during the night; it becomes startled by interior lighting, the television, and other visual or auditory stimuli despite having been exposed to such on a regular basis throughout its life; it seeks less and less of the human attention, praise, and play, and is hesitant to take treats, drink fresh water, or eat fresh food.

The development and validation of tests for assessing cognitive function including discrimination, oddity, reversal, and spatial memory has been instrumental in documenting age-related cognitive differences and the deterioration of such function. The associated neurodegenerative changes include: reduction in brain mass, increased ventricular size, meningeal calcification, demyelization, neuroaxonal degeneration, reduction in neurons, increased accumulation of diffuse beta amyloid plaques with perivascular infiltrates, depletion of catecholamines, increase in monoamine oxidase B (MAOB) activity, resulting in a decline in the cholinergic system. Common clinical signs of cognitive decline in companion pets, such as dogs and cats, are represented by the acronym DISHA (Disorientation, Altered Interactions with people or other pets, Altered Sleep-wake cycles, Housesoiling, Activity changes (initially decline then increased restless or repetitive locomotion).

Little is known about the staging and phenotypic variability of CDS, and little is known in terms of the prevention and treatment of CDS.

As such, there remains a need for compositions and prophylactic treatment regimens that may improve the overall mental condition of non-human animals such as canines and felines, and which may thus delay or otherwise ameliorate a progression of conditions that are associated with or seen during the normal course of non-human animal aging.

SUMMARY OF DISCLOSURE

According to various aspects, the present disclosure relates to a homotaurine-enriched composition for improving a mental condition of a non-human animal, the homotaurine-enriched composition comprising homotaurine and one or more edible materials.

According to various aspects, the present disclosure relates to a kit comprising the homotaurine-enriched composition as defined herein; and a dispensing device for dispensing the homotaurine-enriched composition.

According to various aspects, the present disclosure relates to a homotaurine-enriched supplement for improving a mental condition of a non-human animal, the homotaurine-enriched food supplement comprising an effective amount of homotaurine homotaurine-enriched composition.

According to various aspects, the present disclosure relates to a kit comprising: the homotaurine-enriched supplement as defined herein; and a dispensing device for dispensing the homotaurine-enriched composition.

According to various aspects, the present disclosure relates to the use of a homotaurine or a homotaurine-enriched composition for improving a mental condition of a non-human animal. According to various aspects, the present disclosure relates to the use of a homotaurine or a homotaurine-enriched composition for delaying onset of neurological conditions associated with aging of a non-human animal.

According to various aspects, the present disclosure relates to the use of a homotaurine or a homotaurine-enriched composition for prevention and/or treatment of dementia is a non-human animal.

According to various aspects, the present disclosure relates to the use of homotaurine or a homotaurine-enriched composition for evaluating efficacy of a candidate compound and/or a veterinary candidate formulation and/or veterinary candidate edible materials in the prevention and/or treatment of CDS in a non-human animal.

According to various aspects, the present disclosure relates to the use of a homotaurine-enriched supplement for improving a mental condition of a non-human animal.

According to various aspects, the present disclosure relates to the use of a homotaurine-enriched supplement for delaying onset of neurological conditions associated with aging of a non-human animal.

According to various aspects, the present disclosure relates to the use of a homotaurine-enriched supplement for prevention and/or treatment of dementia is a non-human animal.

According to various aspects, the present disclosure relates to the use of homotaurine-enriched supplement for evaluating efficacy of a candidate compound and/or a veterinary candidate formulation and/or veterinary candidate edible materials in the prevention and/or treatment of cognitive dysfunction syndrome (CDS) in a non-human animal.

According to various aspects, the present disclosure relates to a method for for improving a mental condition of a non-human animal, the method comprising administering an effective amount of a homotaurine or a homotaurine-enriched composition to a non-human animal in need thereof.

According to various aspects, the present disclosure relates to a method for delaying onset of neurological conditions associated with aging of a non-human animal, the method comprising administering an effective amount of a homotaurine or a homotaurine-enriched composition to a non-human animal in need thereof.

According to various aspects, the present disclosure relates to a method for prevention and/or treatment of dementia is a non-human animal, the method comprising administering an effective amount of a homotaurine or a homotaurine-enriched composition to a non-human animal in need thereof.

According to various aspects, the present disclosure relates to the use of an effective amount of homotaurine for prevention or treatment of cognitive dysfunction syndrome (CDS) in a non-human animal, wherein the effective amount of homotaurine is between about 1 g/day and about 5 g/day, between about 500 mg/day and about 5 g/day, between about 500 mg/day and about 2 g/day, between about 500 mg/day and about 1 g/day, between about 250 mg/day and about 500 mg/day, between about 50 mg/day and about 100 mg/day, between about 10 mg/day and about 50 mg/day, or between about 10 mg/day and about 25 mg/day.

DETAILED DESCRIPTION

Figure 1:
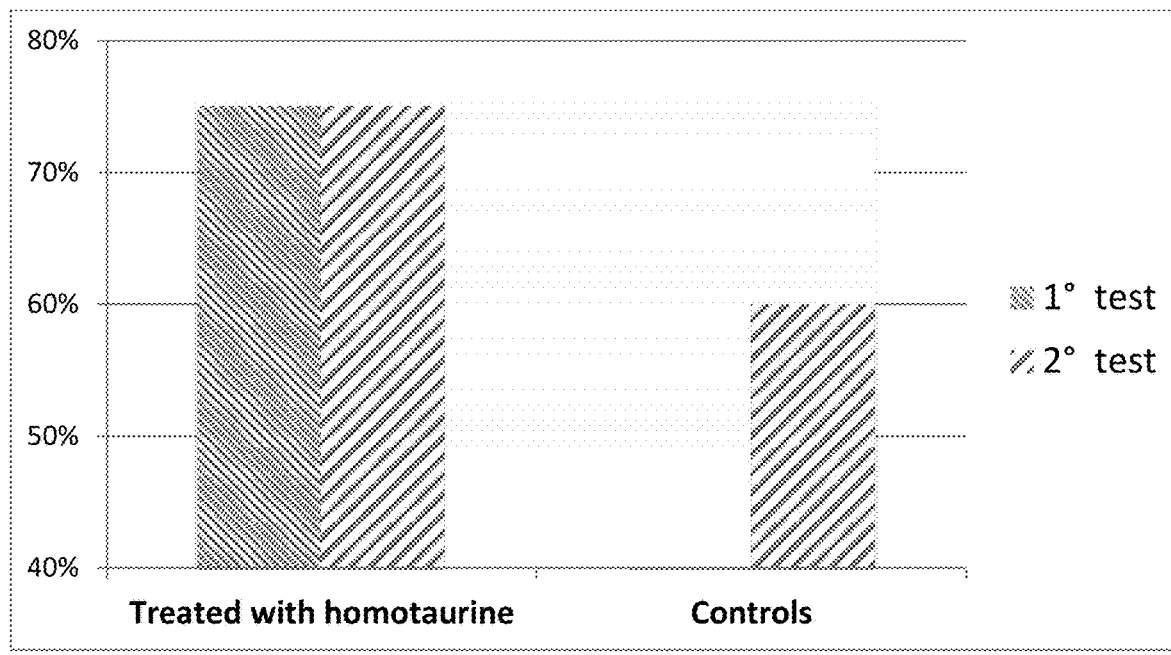
FIG. 1 is a graph showing the percentage of aged dogs who received a composition according to one embodiment of the present disclosure and passed the learning test.

The present disclosure stems from the discovery that administration in non-human animals of homotaurine may be effective as a prophylaxis for avoiding or delaying onset of brain deterioration and loss of mental and/or other cognitive functions, and may be effective for improving the general mental condition and/or general brain function of non-human animals. In some embodiments, homotaurine and compositions comprising homotaurine as defined herein may be useful to achieve one or more of the following: i) improvement of the overall mental wellness and/or the overall mental health of a non-human animal; ii) improvement and/or protection of the brain structure and/or function in a non-human animal; and iii) delay of the onset of and/or treatment of CDS.

As used herein, the term "preventing" or "prevention" or "prophylaxis" refers at least to the reduction of likelihood of the risk of (or susceptibility to) acquiring a disease, disorder or condition (i.e., causing at least one of the clinical symptoms of the disease, disorder or condition not to develop, or slow down or delay onset, in a non-human animal that may be exposed to or predisposed to the disease but does not yet experience or display symptoms of the disease).

As used herein, the term "treating" or "treatment" of any disease, disorder or condition refer, in some embodiments, to ameliorating the disease, disorder or condition (i.e., arresting or reducing the development of the disease or at least one of the clinical symptoms thereof). In certain instances, "treating" or "treatment" refers to ameliorating at least one physical parameter, which may or may not be discernible by the non-human animal. In certain instances, "treating" or "treatment" refers to inhibiting the disease, disorder or condition, either physically (e.g., stabilization of a discernible symptom), physiologically (e.g., stabilization of a physical parameter), or both. In certain instances, "treating" or "treatment" refers to delaying the onset of the disease, disorder or condition. The term "treating" refers to any indicia of success in the treatment or amelioration of an injury, pathology or condition, including any objective or parameter such as abatement; remission; diminishing of symptoms or making the injury, pathology or condition more tolerable to the non-human animal; slowing in the rate of degeneration or decline, making the final point of degeneration less debilitating; improving a non-human animal's physical or mental well-being; improving and/or preserving memory and cognitive functions; restoring and/or improving mental alertness or, in some situations, preventing the onset of dementia.

In some embodiments, homotaurine and compositions comprising homotaurine as defined herein may be useful for protecting the brain structure, for preserving memory, for sustaining brain cell health in a non-human animal.

In some other embodiments, homotaurine and compositions comprising homotaurine as defined herein may be useful for prevention and/or treatment of CDS in a non-human animal.

The present disclosure also relates to the use of homotaurine and compositions comprising homotaurine for providing neuroprotection to a non-human animal comprising administering to the animal an effective amount of homotaurine or compositions comprising homotaurine as defined herein, such that neuroprotection is provided to the animal.

The present disclosure further relates to the use of homotaurine and compositions comprising homotaurine as defined herein in the treatment or prevention of inflammation in the brain, neuronal cell toxicity, neuronal cell death or neuronal cell loss in a non-human animal having a condition or disease in which Aβ amyloidogenic proteins or peptides are present, or being susceptible or predisposed to said condition or disease, including a disease or condition characterized by Aβ deposition, as well as in the treatment or prevention of diseases and conditions that may be equivalent to maladies in humans such as Alzheimer's disease, cerebral amyloid angiopathy, Down's syndrome, and other human maladies that are manifested in a manner equivalent to cognitive dysfunction syndrome occurring in a non-human animal.

As used herein, the expression "non-human animal" includes, but is not limited to, a canine species, a feline species, a rodent species, or an ungulate species. In some instances, the canine species is a breed of canine that is selected from a large-size companion breed, a medium-sized companion breed or a small-sized companion breed of dog. In some instances, the breed of canine is a pure-breed dog. In some instances, the feline species is selected from a companion feline species. In some instances, the rodent species is selected from a mouse, a rat, a hamster, or a ferret. In some instances, the ungulate species is selected from a bovine, an equine, a porcine, or an *ovis* or ovine animal. Examples of non-human animal also include but are not limited to, pigs, horses, sheeps, goats, cows, birds, rabbits, apes (e.g., monkeys, chimpanzee, and the like) and the like.

In some embodiments, the non-human animal is a companion animal. The expression "companion animal" used in the present disclosure includes any non-human animal suitable for being kept as a pet by humans including without limitation, a dog, a cat, rabbit and a rodent. The term "dog" includes those dogs which are companion animals such as *Canis familiaris*, working dogs and the like. The term dog is synonymous with the term canine. The term "cat" includes those cats which are companion animals known as domestic cats or house cats, or *Felis domesticus*. The term cat is synonymous with the term feline.

As used herein, the term "homotaurine" and equivalent expressions refers to 3-amino-1-propanesulfonic acid, its zwitterionic form (inner salt), and salts and solvates thereof. The homotaurine may be of natural source (extracted or purified from a natural source, e.g. a seaweed) or may be synthetic (e.g. prepared synthetically on site or provided by a commercial source). The term further includes natural extracts containing at least 10%, at least 20%, at least 30%, at least 40%, at least 50%, at least 60%, at least 70%, at least 80%, at least 85%, at least 90%, at least 95%, at least 98%, or at least 99% of homotaurine in the dried extract. In general, the homotaurine may be hydrated or solvated. The homotaurinemay exist in multiple crystalline or amorphous forms.

A "nutraceutically acceptable salt", "acceptable salt" or "suitable salt" of a compound means a salt of a compound that is acceptable for non-human animal consumption. Desirable salts of a compound, for example, will retain or improve the biological and/or chemical and/or physical properties of the free acid of homotaurine as defined herein, and will not be biologically or otherwise undesirable. Salts include base addition salts formed by the replacement of the acidic proton of the sulfonic acid of homotaurine by, for example, a metal ion, including, an alkali metal ion (e.g., lithium, sodium, potassium), an alkaline earth ion (e.g., magnesium, calcium, barium), or other metal ions such as aluminum, zinc, iron and the like; or by an organic base such as ammonia, ethylamine, diethylamme, ethylenediamine, ethanolamine, diethanolamine, triethanolamine, tromethamine, N-methylglucamine, piperazine, chloroprocain, procain, quaternary ammoniums (e.g. L-carnitine, L-carnitine alkanoyl derivatives such as acetyl, propionyl and butyryl-L-carnitine, choline, choline derivatives such as acetylcholine, butyrylcholine, propionylcholine, other aliphatic esters of choline, fatty acid esters of choline such as eicosapentaenoyl (EPA), docosahexaenoyl (DHA), docosapentaenoyl (DPA), capryloyl, lauroyl, myristoyl, palmytoyl, stearoyl, oleoyl, ricinoleoyl, linoleoyl, alpha-linolenoyl, and arachidonoyl, phosphorylcholine, phosphatidylcholines, trimethylglycine, and the like), amino acids (e.g. L-arginine, L-lysine, histidine, and the like), amine-containing or polyamine compounds (e.g., putrescine, spermidine, spermine, galanthamine, dimethylaminoethanol, and the like), vitamins having a basic group (e.g., vitamins B1 (thiamine), B2 (riboflavin), B3 (niacin or nicotinic acid), B4 (adenine), B6 (pyridoxine), B12 (cobalamine), vitamin U (S-methylmethionine) or folic acid), alkaloids (e.g., huperzine A and tetrandnne), and the like.

Acceptable salts may be prepared from the parent agent by conventional chemical methods. Generally, such salts are prepared by reacting the free base forms of the counterion with a stoichiometric amount of the acid form of homotaurine (or its zwitterion) in water or in an organic solvent, or in a mixture of the two. Salts may be prepared in situ, during the final isolation or purification of the agent or by separately reacting homotaurine in its free acid or zwitterion form with the desired corresponding base, and isolating the salt thus formed.

All acid, salt, base, and other ionic and non-ionic forms of homotaurine are included in the described compositions, formulation, methods and uses of the present disclosure. For example, if homotaurine is shown as an acid herein, its salt and zwitterionic forms are also included. Likewise, if homotaurine is shown as a salt, the acid and/or zwitterionic forms are also included.

The expression "reduction of side effects of homotaurine" refers to decreasing the amount of or severity of one or more side effects of homotaurine by, e.g., 5%, 10%, 20%, 30%, 40%, 50%, 60%, 70%, 80%, 90%, 95%, 99%, or 99.9%, or even 100%, which decrease is with respect to the amount of or severity of a side effect of homotaurine that is exhibited when the same equivalent molar dose of homotaurine is administered orally in water solution or in an immediate release solid formulation (e g. lose-filled capsules).

"Nutraceutically acceptable" or simply "acceptable" associated with a term such as salts, inert ingredients, carriers, excipients, additives, ingredients, etc., refers to salts, inert ingredients, carriers, excipients, additives, ingredients, etc., suitable for use in contact with the tissues of non-human animals without undue toxicity, incompatibility, instability, irritation, and the like, commensurate with a reasonable benefit/risk ratio.

"Acceptable vehicle" or "nutraceutically acceptable vehicle" and equivalent expressions refer to a diluent, adjuvant, excipient, or carrier with which a material is administered.

In general, the term "composition" and equivalent expressions refer to an enriched/supplemented materials of the present disclosure in a form ready for administration or for consumption. The term composition equally includes, for example, nutraceutical compositions, food additives and food preparations (foodstuffs). The expressions "nutraceutical", "nutraceutical composition", "dietary supplement" or "dietary composition", "food supplement", "nutritional composition" or "nutritional supplement" and equivalent expressions refer to an enriched/supplemented material of the present disclosure, optionally in combination with at least one nutraceutically acceptable vehicle, in a form suitable for administration of the material and compound therein to a non-human animal, e.g., tablets, capsules, etc. The expression "food additive" refers to an enriched/supplemented edible material of the present description in a form ready to be used in the preparation of foodstuffs, such as powders to be added in the process of making foods, or as a ready-to-use powder form to be added to prepared food or feed. The terms "foodstuff", "food compositions" or "food preparations" refers to an enriched/supplemented edible material of the present disclosure in a form that can be consumed, for example, eaten, drank, or ingested by a non-human animal.

In some embodiments of the present disclosure, homotaurine may be replaced by homotaurine analogs. As used herein, the expression "homotaurine analogs" includes any homotaurine analogs that retain the activity of homotaurine as defined herein. The homotaurine analogs useful in the compositions and methods of the present disclosure can achieve one or more of the following: i) improvement of the overall mental wellness and/or the overall mental health of a non-human animal; ii) improvement and/or protection of the brain structure and/or function in a non-human animal; and iii) delay of the onset of and/or to treat CDS. It will be understood that homotaurine analogs are compounds that have structural similarity with homotaurine; but differ by at least one structural element. Examples of homotaurine analogs include, but are not limited to, taltrimide, calcium acamprosate and tauromustine.

In some embodiments of the present disclosure, the homotaurine is in a form suitable for administration to a non-human animal (e.g, powder, pills, caplets, liquid, gel, cream, spray, or the like). In some instances, the homotaurine is a form suitable for oral, intravenous, subcutaneous, transdermal, topical, buccal, sublingual, nasal, inhalation, pulmonary, or parenteral delivery according to conventional methods known in the art. In some specific embodiments, homotaurine is in a form suitable for oral administration or consumption (e.g, liquid, powder, capsule, pill, or the like).

As used herein the expressions "effective amount" or "nutraceutically effective amount" refers to the amount of enriched/supplemented material or composition or its content in homotaurine, upon single or multiple administration to or consumption by the non-human animal, which provides the desired effect to the non-human animal. An effective amount can be readily determined by the use of known techniques and/or by observing results obtained under analogous circumstances. In determining the effective amount administered, a number of factors are considered, including, but not limited to the size, age, and general health of the non-human animal, the specific disease or condition involved, the degree, involvement, or severity of the disease or condition the response of the individual non-human animal, the mode of administration, the bioavailability characteristics of the preparation administered, the use of concomitant medication, and other relevant circumstances. The effective amount refers to an amount of the material, composition or food preparation or its content in homotaurine to obtain significant benefit to the non-human animal, either by providing neuroprotection, protecting memory function, protecting the brain structure associated with memory and learning, by preserving memory, by sustaining brain cell health, by maintaining cognitive functions in the non-human animal. The expression "lessening metabolism of homotaurine" (or related terms such as reduction, less, lowering, reducing, lowered, etc.) refers to decreasing the degree or amount of first-pass metabolism in the GI tract or liver of homotaurine by e.g., 5%, 10%, 20%, 30%, 40%, 50%, 60%, 70%, 80%, 90%, 95%, 99%, or even 100%, which decrease is with respect to the degree or amount of metabolism of homotaurine that occurs when the same equivalent molar dose of homotaurine is administered orally in a water solution.

Amounts of homotaurine to be administered to the non-human animal in an administration regimen may include a per dose amount in a gram or milligram range or lesser amounts of homotaurine (in the compositions of the present disclosure) per kilogram of the non-human animal depending on the species, breed, age and size of the non-human animal. Amounts of homotaurine to be administered to the non-human animal in dosing administration regimen may be calculated on a basis of the non-animal weight (e.g., about 50 micrograms per kilogram to about 500 milligrams per kilogram, about 1 milligram per kilogram to about 200 milligrams per kilogram, about 1 milligram per kilogram to about 100 milligrams per kilogram, about 1 milligram per kilogram to about 50 milligram per kilogram, about 1 milligram per kilogram to about 10 milligrams per kilogram, or about 3 milligrams per kilogram to about 5 milligrams per kilogram).

Additional examples of doses of homotaurine, depending on the species, breed, age and size of the non-human animal, may include doses of between about 1 gram and about 5 g, between about 500 mg and about 2 g, between about 500 mg and about 1 g, between about 200 mg and about 500 mg, between about 200 mg and about 250 mg, between about 25 mg and about 200 mg, between about 5 mg and about 500 mg, between about 25 mg and about 300 mg, between about 50 mg to about 150 mg, between about 10 mg and about 100 mg, between about 20 mg and about 75 mg, between about 10 mg and about 50 mg, about 5 g, about 4 g, about 3 g, about 2 g, about 1 g, about 500 mg, about 250 mg, about 100 mg, about 50 mg, or about 10 mg, preferably, once daily or twice daily.

Additional examples of doses of homotaurine, depending on the species, breed, age and size of the non-human animal, may include doses of between about 1 g/day and about 5 g/day, between about 500 mg/day and about 5 g/day, between about 500 mg/day and about 2 g/day, between about 500 mg/day and about 1 g/day, between about 250 mg/day and about 500 mg/day, between about 50 mg/day and about 100 mg/day, between about 10 mg/day and about 50 mg/day, or between about 10 mg/day and about 25 mg/day.

For comparison, examples of doses for homotaurine per se can include between about 200-500 miligram of homotaurin per kiligram of non-human animal (once daily), between about 100-250 milligram of homotaurin per kilogram of non-human animal (once daily), between about 10-50 milligram of homotaurin per kilogram of non-human animal (once daily), between about 1-2 milligram of homotaurine per kilogram of non-human animal (twice daily) or between about 4-6 milligram of homotaurine per kilogram of the non-human animal (daily).

A person skilled in the art will appreciate that the effective amount of homotaurine to be administered depends on the type of a non-human animal into which the homotaurine is to be administered and/or the physical size of the non-human animal and/or the age of the non-human animal.

In some embodiments, homotaurine may be administered directly to the non-human animals. That is to say that, in such embodiments, homotaurine is not mixed with any other materials prior to being administered to the non-human animals.

In some other embodiments however, homotaurine may be mixed with or added to other materials prior to administration to the non-human animals to form a homotaurine-enriched composition. The homotaurine-enriched composition when given or administered to the non-human animals may provide prophylaxis of mental deterioration of the non-human animal and may improve the overall mental wellness and/or the overall mental health of a non-human animal.

As used herein, the expression "homotaurine-enriched composition" or "homotaurine-supplemented composition" and equivalent expressions refers to a composition in which the content in homotaurine is higher than the content naturally occurring in the sum of the other materials of the composition. Prior to enrichment/supplementation, the materials' content in homotaurine does not amount to an effective amount of homotaurine.

In some embodiments, the composition of the present disclosure comprises between about 0.1% and about 60%, 0.2% and about 60%, between about 0.1% and about 50%, between about 0.1% and about 10%, between about 0.5% and about 50%, between about 1% and about 40%, between about 1% and about 20%, between about 1% and about 10%, between about 10% and about 40%, between about 10% and about 30%, or between about 20% and about 40% of homotaurine by weight of the composition.

In some other embodiments, the composition of the present disclosure comprises between about 0.001% and about 15%, of homotaurine by weight of the composition on a dry matter basis. In some other instances, the composition comprises less than about 60%, less than about 50%, less than about 40%, less than about 30%, less than about 25%, less than about 15%, less than about 10%, less than about 5%, less than about 2%, less than about 1%, less than about 0.5%, less than about 0.2%, less than about 0.1%, less than about 0.01%, less than about 0.001% of homotaurine by weight of the composition on a dry matter basis.

As indicated above, the compositions of the present disclosure may comprise materials other than homotaurine (i.e., additional materials). In the instances where the composition is for oral administration, the additional materials may be edible materials and homotaurine may be mixed or added to one or more edible materials.

In some instances, the additional materials are present in the composition at an amount of between about 40% and about 99.8%, between about 50% and about 99.5%, between about 60% and about 99% between about 80% and about 99%, between about 90% and about 99%, between about 60% and about 90%, between about 70% and about 90%, or between about 60% and about 80% by weight of the composition.

Examples of additional edible materials include, but are not limited to a protein source, a carbohydrate source, a fat source, a vegetable source, a vitamin source, balancing agents and the like. Examples of proteins sources, carbohydrate sources, fat sources, vitamin sources, minerals sources, balancing agents, and the like, suitable for inclusion in the compositions of the present disclosure may be selected from among those conventional materials known to those of ordinary skill in the art.

Proteins useful as ingredients of the compositions of the present disclosure include, but are not limited to, meat protein isolate, whey protein isolate, mixtures thereof, and the like, as well as vegetable sources, such as soy protein isolate, corn, wheat gluten, mixtures thereof, and the like. Additional sources of protein may include one or more of the following: animal proteins, including mammalian, avian protein, reptilian, amphibian, fish, invertebrate proteins and combinations thereof; e.g., from any of cattle, sheep, pig, goat, deer, rabbit, horse, kangaroo, their milk, curds, whey or blood, and internal tissues and organs such as smooth muscle, striate muscle, liver, kidney, intestine or heart; additional avian protein sources encompass turkey, goose, duck, ostrich, quail, pigeon, their eggs and internal tissues and organs such as smooth muscle, striate muscle, liver, kidney, intestine or heart; amphibian sources include frog or salamander, reptilian protein sources include alligator, lizard, turtle and snake; a fish protein sources include catfish, herring, salmon, tuna, bluefish, cod, halibut, trout, swordfish and their eggs; and an invertebrate protein sources include lobster, crab, clams, mussels or oysters, and combinations thereof Carbohydrate components of the compositions of the present disclosure may, in addition to one or more of brown rice and oat groats, be from any source, and may enter the food composition as part of another ingredient, such as the protein source. In certain embodiments, carbohydrates useful as ingredients of the food compositions of the present invention include polysaccharides (e.g., starches and dextrins) and sugars (e.g., sucrose, lactose, maltose, glucose, and fructose) that are metabolized for energy when hydrolyzed. Examples of additional carbohydrate sources suitable for inclusion in the compositions disclosed herein include, but are not limited to, corn, whole yellow corn, grain sorghum, wheat, barley, and rice.

Fats useful as ingredients of the compositions of the present disclosure may be from any source, such as but not limited to poultry fat, beef tallow, lard, choice white grease, soybean oil, corn oil, canola oil, sunflower oil, mixtures thereof, and the like. The fat may be incorporated completely within the food composition, deposited on the outside of the food composition, or a mixture of the two methods.

In other embodiments, the composition of the present disclosure is a nutritionally complete diet for a companion animal, e.g., a canine or a feline companion animal. In a specific aspect of this embodiment, the composition is a food product and the food product is a nutritionally complete diet formulated for a canine or feline companion animal.

In other embodiments, the homotaurine to be administered is formulated and prepared as a supplement. Supplements include, for example, a food product, feed, or pet food, that can be used with another food product, feed, or pet food composition to improve the nutritive balance or performance of the total. Contemplated supplements include compositions that are fed undiluted as a supplement to other feeds or pet foods, offered free choice with other parts of a non-human animal's ration that are separately available, or diluted and mixed with a non-human animal's regular feed or pet food to produce a complete feed or pet food. Supplements may be in various forms including, for example, powders, liquids, syrups, pills, encapsulated compositions, sprays, or the like.

In some embodiments of the present disclosure, homotaurine may be used in combination with at least one other component that is effective in the prevention and/or treatment of CDS. Such other or second component may include, but is not limited to, a monoamine oxidase inhibitor such as, but not limited to, Selegiline™ (licensed in North America for treatment of cognitive dysfunction syndrome in dogs). Other components that may be considered include, L-deprenyl hydrochloride, phosphatidylserine, pyridoxine, S-adenosyl-L-methionine, flavonoids, *Ginko biloba* extract, resveratrol and δ-alpha-tocopherol, botanical oils, medium-chain triglycerides (MCT), memantine, amantadine, adranafil, modafinil, vitamin E, vitamin A, Senilife™ (which is a combination of phosphatidylserine, pyridoxine, *Gingko biloba* extract, resveratrol and δ-alpha-tocopherol), Neutricks™ (which contains apoaequorin, a substance derived from jellyfish). Other supplements may also be considered to be used in combination with homotaurine, such as coconut oil, omega-3 fatty acids and *Gingko biloba*.

Selegiline is a monoamine oxidase B inhibitor that may improve the signs of CDS by enhancing dopamine and other catecholamines in the cortex and hippocampus and by decreasing free radical load.

Propentofylline, which is licensed in Europe and Australia for the treatment of dullness, lethargy, and depressed demeanor in old dogs, may increase blood flow and inhibit platelet aggregation and thrombus formation.

A number of natural products, including diets and supplements, have also been shown to have beneficial effects in improving the signs and potentially slowing cognitive decline. Two such diets are Canine B/d®, which is supplemented with fatty acids, antioxidants, and DL-alpha-lipoic acid and L-carnitine to enhance mitochondrial function, and a specialized Purina One® diet that uses botanic oils containing medium-chain triglycerides to provide ketone bodies as an alternative source of energy for aging neurons.

Other natural supplements that have demonstrated efficacy in improving cognitive function include Activait®, which contains phosphatidylserine in combination with α-lipoic acid, carnitine, fatty acids, glutathione, and other antioxidants; S-adenosyl-L-methionine (Novifit®); and apoaequorin (Neutricks®), a calcium-buffering protein found in jellyfish. In some instances, any of the aforementioned diets and supplements may be combined with a composition or formulation of the present disclosure for administration to the non-human animal in order to provide for the prophylaxis of mental deterioration of the non-human animal and to improve the overall mental wellness and/or the overall mental health of the non-human animal.

In some embodiments, homotaurine may be absorbed into the edible material which is to be fed to the non-human animals.

The compositions of the present disclosure, which are to be administered to non-human animals, may be prepared as food products suitable for consumption by the non-human animals. These food products may be of any consistency or moisture content; i.e., the compositions of the present invention may be moist, semi-moist, or dry food products. "Moist" food products are generally those with moisture content of from 60% to 90% or greater. "Dry" food products are generally those with a moisture content of from 3% to 11%, and are often manufactured in the form of small pieces or kibbles. "Semi-moist" food products generally have a moisture content of from 25% to 35%.

In certain embodiments, the food products may be prepared in a canned or wet form using conventional food preparation processes known to those of ordinary skill in the art.

In other embodiments, the food products may be prepared in a dry form using convention processes known to those of ordinary skill in the art.

In preparing a composition as defined in the present disclosure, any material generally may be incorporated into the composition during the processing of the formulation, e.g., during and/or after mixing of the other materials of the composition. Distribution of these materials into the composition can be accomplished by conventional means. In certain embodiments, ground animal and/or poultry proteinaceous tissues are mixed with other ingredients, including nutritional balancing agents, inorganic salts, and may further include cellulose, bulking agents and the like, along with sufficient water for processing.

In particular embodiments, the compositions are formulated so as to be easier to chew. In specific embodiments, the compositions and food products are formulated to address specific nutritional differences between species and breeds of animals, as well as one of more of the attributes of the animal. For example, canine and feline foods, for example, are typically formulated based upon the life stage, age, size, weight, body composition, and breed.

In some embodiments, the homotaurine is formulated with materials and/or ingredients which together transiently maximizes the degradation and/or the release of the homotaurine from the edible materials into the stomach and/or the intestine of the non-human animal and transiently maximises the absorption of the homotaurine by the stomach and/or the intestine of the non-human animal. For example, dried seaweed may be hydrated in a solution comprising between about 1 g and about 75 g of homotaurine per 100 ml of water, preferably between about 5 g and about 50 g per 100 mL of water. The seaweed absorbs part of the homotaurine from the solution within or proximate its cells. The enriched/supplemented seaweed is then optionally dried with or without being previously rinsed with fresh water. The drying process is accomplished using any food-processing technique known to the skilled in the art, e.g. through lyophilization, or heating with or without the use of vacuum.

An homotaurine and the composition comprising homotaurine of the present disclosure may also be formulated into an equivalent of a human nutraceutical composition prior to administration using techniques and procedures well known in the art.

Compositions of the present disclosure for oral administration to non-human animals may further comprise, without limitation, any non-allergenic or non-immunogenic carrier or diluent suitable for oral administration routes to the particular non-human animal species and/or breed of non-human animal. Such Compositions of the present disclosure for oral administration may be in the form of capsules (e.g. hard or soft shell gelatin capsule), tablets, powders, granules, pellets, e.g., coated (e.g., films or enteric coatings) or uncoated, each containing a predetermined amount of a material of the present disclosure as an active ingredient. Alternatively, compositions of the present disclosure suitable for oral administration may be in the form of pre-shaped foodstuff (for example, dried dog or cat food/kibble) that comprises a dosage of homotaurine for each piece or unit of dried food/kibble and which may be administered to the non-human animal as part of a daily/weekly/monthly feeding regimen for the non-human animal. The daily/weekly/monthly feeding regimen may comprise a schedule of foodstuff weight per feeding to be administered in order to deliver and maintain an adequate level of homotaurine in the non-human animal over a period of time during the growth and development of the non-human animal and so as to provide for a prophylactic treatment of CDS in the non-human animal.

In solid dosage forms for oral administration, which may be included for example as an added or an integral part of a foodstuff formulation for the particular species or breed of a non-human animal of the disclosure, the homotaurine of the present disclosure may be, for example, mixed with one or more acceptable carriers (depending on the animal health care laws, regulations or equivalent provisions of the given country), such as sodium citrate or dicalcium phosphate, or any of the following: fillers or extenders, such as starches, lactose, sucrose, glucose, mannitol, or silicic acid, binders, such as, for example, carboxymethylcellulose, alginates, gelatin, polyvinyl pyrrolidone, sucrose or acacia, humectants, such as glycerol; disintegrating agents, such as agar-agar, calcium carbonate, potato or tapioca starch, alginic acid, certain silicates, and sodium carbonate, solution retarding agents such as paraffin, absorption accelerators such as quaternary ammonium compounds, wetting agents, such as, for example, cetyl alcohol and glycerol monostearate, absorbents, such as kaolin and bentonite clay, lubricants, such as talc, calcium stearate, magnesium stearate, solid polyethylene glycols, sodium lauryl sulfate, and mixtures thereof, coloring agents buffering agents and/or flavoring agents.

Prevention of the action of microorganisms can be achieved by various antibacterial and antifungal agents for example, parabens, chlorobutanol, phenol, ascorbic acid, thimerosal, and the like. Other compositions useful for attaining systemic delivery of the non-human animal agents include sublingual and buccal dosage forms. Such compositions typically comprise one or more of soluble filler substances such as sucrose, sorbitol and mannitol, and binders such as acacia, microcrystalline cellulose, carboxymethyl cellulose and hydroxypropyl methyl cellulose Glidants, lubricants sweeteners, colorants, antioxidants and flavoring agents disclosed above may also be included. Under ordinary conditions of storage and use, these preparations may contain a preservative to prevent the growth of microorganisms.

The composition of the present disclosure may be packaged as part of a kit, optionally including a container (e.g., packaging, a box, a vial, and the like.). The kit may comprise the composition as defined herein together with instructions on how to use the composition as defined herein. The kit may further comprise a dispensing device for dispensing a suitable amount of the composition as defined herein to the non-human animal. The dispensing device may be for example, a measuring cup, a measuring spoon, and the like.

In certain embodiments of the present disclosure, the non-human animal is prognosed to benefit from the methods of the present disclosure, and is selected based on this need. A non-human animal in need includes animals that have been identified as having CDS or as having a disease, disorder or condition related to β-amyloid deposition (or a deposition of other neurologically damaging molecules, peptides, proteins or molecular complexes or degradation products that may be associated with an onset and/or progression of CDS (or an equivalent condition) in the non-human animal), as the non-human animal may be exhibiting a symptom or symptoms of such a disease or disorder, or is at risk of such a disease or disorder due to the breed of the non-human animal, and thus may be expected, based on a prognosis or diagnosis, to benefit from treatment in accordance with the present disclosure (e.g., curing, healing, preventing, alleviating, relieving, altering, remedying, ameliorating, improving, or affecting the disease or disorder, the symptom of the disease or disorder, or the risk of the disease or disorder).

Another aspect of the present disclosure pertains to a method for inhibiting neuronal cell death in a non-human animal by administering an effective amount of a homotaurine enriched/supplemented material or composition of formulation of the present disclosure. In yet another aspect, the present disclosure pertains to a method for providing neuroprotection to a non-human animal having an Aβ-amyloid-related disease or condition which includes the step of administering to (or consuming by) a non-human animal, an effective amount of a material or composition or formulation of the present disclosure, such that neuroprotection is provided. As used herein, the term "neuroprotection" includes protection of neuronal cells of a non-human animal from cell death that may result in initiation of processes such as, but not limited to: the destabilization of the cytoskeleton; DNA fragmentation; the activation of hydrolytic enzymes, such as phospholipase A2; activation of caspases, calcium-activated proteases and/or calcium-activated endonucleases; inflammation mediated by macrophages; calcium influx into a cell; membrane potential changes in a cell; the disruption of cell junctions leading to decreased or absent cell-cell communication; and the activation of expression of genes involved in cell death.

The materials, compositions and formulations of the present disclosure may act to ameliorate the onset or course of a disease or condition using any of the following mechanisms (this list is meant to be illustrative and not limiting): protecting neurons from induced neuronal toxicity, slowing the rate of β-amyloid fibril formation or deposition and/or the formation or deposition of other neurologically damaging molecules, peptides, proteins or molecular complexes or degradation products that may be associated with an onset and/or progression of CDS (or an equivalent condition) in the non-human animal; lessening the degree of β-amyloid deposition or deposition of other neurologically damaging molecules, peptides, proteins or molecular complexes or degradation products that may be associated with an onset and/or progression of CDS (or an equivalent condition) in the non-human animal; inhibiting, reducing, or preventing amyloid or similar fibril formation; inhibiting neurodegeneration or cellular toxicity induced by β-amyloid or other neurologically damaging molecules, peptides, proteins or molecular complexes or degradation products that may be associated with an onset and/or progression of CDS (or an equivalent condition) in the non-human animal; inhibiting amyloid-induced inflammation in the brain or brain inflammation induced by other neurologically damaging molecules, peptides, proteins or molecular complexes or degradation products that may be associated with an onset and/or progression of CDS (or an equivalent condition) in the non-human animal; enhancing the clearance of β-amyloid from the brain or the clearance of other neurologically damaging molecules, peptides, proteins or molecular complexes or degradation products that may be associated with an onset and/or progression of CDS (or an equivalent condition) in the non-human animal; enhancing degradation of Aβ in the brain or the degradation of other neurologically damaging molecules, peptides, proteins or molecular complexes or degradation products that may be associated with an onset and/or progression of CDS (or an equivalent condition) in the non-human animal, or favoring clearance of amyloid protein (or neurologically damaging molecules, peptides, proteins or molecular complexes or degradation products that may be associated with an onset and/or progression of CDS (or an equivalent condition) in the non-human animal) prior to its of their organization in fibrils, and decreasing the ratio of Aβ42:Aβ40 in the CSF or plasma. As well, as alterations in neurotransmitters can lead to behavior changes such as increased irritability, agitation, fear, decreased responsiveness to stimuli, and altered sleep-wake cycles, the materials, compositions and formulations of the present disclosure may also be helpful in improving the mood and the behavior related to CDS occurrence as homotaurine can act as a GABA agonist.

In another embodiment, the present disclosure pertains to a method for improving or preserving cognition function in a non-human animal. The method includes administering an effective amount of a material or composition or formulation of the present disclosure, such that the non-human animal's cognition function is improved or preserved.

Improvement or protection of cognition or memory is present within the context of the present disclosure if there is a measurable difference between the performances of non-human animals treated using the methods of the present disclosure as compared to members of a placebo group historical control, or a group using a non-enriched/supplemented equivalent material, or between subsequent tests given to the same non-human animal.

In certain embodiments, compositions of the present disclosure may be administered concurrently with the administration of at least one therapeutic or another nutraceutical agent, which can be part of the same composition as, or in a different composition from, that containing the materials of the present disclosure. In certain embodiments, the therapy or dosing administration regimen may comprise alternating between administering a composition or formulation of the present disclosure and a composition comprising at least one therapeutic or another nutraceutical agent, e.g., to minimize adverse side effects associated with a particular agent.

In some other embodiments, homotaurine and the compositions comprising homotaurine of the present disclosure may be used as a measurable indicator of the efficacy of a candidate compound or a candidate composition/formulation or a candidate edible material in improving the general mental condition and/or general brain function of a non-human animal. In some other embodiments, homotaurine and the compositions comprising homotaurine of the present disclosure may be used in determining or assessing the efficacy of a candidate compound or a candidate composition/formulation or a candidate edible material in improving the general mental condition and/or general brain function of a non-human animal. In these embodiments, homotaurine and the compositions comprising homotaurine of the present disclosure may be used as a positive control against which the efficacy of the new candidate is assessed. In such embodiments, the efficacy of the candidate compound or a candidate composition/formulation or a candidate edible material in improving the general mental condition and/or general brain function of a non-human animal is compared to the efficacy of homotaurine or the compositions comprising homotaurine of the present disclosure in that same non-human animal. If the efficacy of the candidate is the same or is higher than the efficacy of the homotaurine or the compositions comprising homotaurine of the present disclosure, than the candidate is shown to improve the general mental condition and/or general brain function of a non-human animal.

EXAMPLES

Example 1: Example of an Operating Protocol in Animal Subjects

The study on animal subjects will be conducted in the following fashion:
- 2 groups of older animals, over the age of 10 years, males and females, each consisting of 15 subjects; a group will be treated with test product, homotaurine at a dose of 1 g/subject PO SID (orally, once daily), and one will represent the control group;
- 2 groups of young animals about 5 years of age, males and females, each consisting of 5 subjects; a group will be treated with test product, homotaurine at a dose of 1 g/subject PO SID (orally, once daily), and one will represent the control group.

The opportunity to enlist even younger subjects will be dictated by two factors: a) verify how learning changes between young animals and older animals; and b) check if the supplement as effects only in older animals or even in young animals.

All subjects will be followed for eight months, with the following methodological scheme:

T0: (prior to administration of the test product)
  Specialized clinical examination
  Behavioral assessment
  Learning test
  Blood test (complete blood count, blood chemistry, dopamine determination, β-amyloid peptides determination)

T1: (after 2 weeks of administration of the test product)
  Retention test and Reversal learning test T2: (after 4 months of administration of the test product)
Behavioral assessment
Learning test T3: (after 2 weeks from T2)
Retention test and Reversal learning test T4: (after 8 months of administration of the test product)
Behavioral assessment
Learning test
Blood test (complete blood count, blood chemistry, dopamine determination, β-amyloid peptides determination)

T5: (after 2 weeks from T4)
Retention test and Reversal learning test

Behavioral assessment: the behavioral assessment of each dog will be carried out in order to classify on a scale from 1 to 5 the exploration behavior, the presence of passive behaviors, the spatial orientation ability, the interaction with people, the presence/type of vocalizations and the deletions.

Learning test: the learning test will be conducted in a test apparatus (T-maze). In this test is required to learn which of the two arm choices results in the correct exit path from the apparatus. Each dog will be tested until it achieves the learning criterion of the three consecutive correct trials within the maximum of 15 attempts.

Retention test: this retention test will be performed 2 weeks after the learning task with the aim to assess if dogs retained the acquired information. The dogs will pass the retention test if entering the correct lateral arm, as acquired during the learning phase, at least three out of the four trials.

Reversal learning test: this reversal learning test will take place only if the dog successfully passed the retention test and immediately after it. This test is intended to evaluate the dog's ability to contrast and modify previously acquired behavioral responses. The protocol and learning criterion are the identical of the learning task, but the arm choice resulting in a path out of the apparatus is reversed.

The dogs' responses will be monitored in real time using video camera and the data will be also recorded.

Example 2

The experiment began by selecting two groups of elderly dogs (age more than 10 years, 16 subjects per group) and two groups of young adult dogs (between 3 and 6 years of age, 6 subjects per group), who were divided randomly balancing them per age, seniority, and size.

The dogs underwent a cognitive learning tests (Spatial reversal learning is impaired by aging in pet dogs, P. Mongillo et al., Age, 2013, 35 (6): 2273-2282), in a simple maze built to this trial. Passing the test consisted in the dog's ability to learn to get out of the labyrinth in the direction that he himself had chosen in the first successful attempt. The number of attempts has been the test score: the lower the number of attempts, better cognitive performance. Immediately after the test, two groups of dogs (one old and one young) started to receive food integration of homotaurine capsules.

Homotaurine at was administered orally once daily (PO SID) at a dose of 1 g/subject.

After 15 days the dogs underwent a memory test (learning result application of first test) and, if they have passed the test, to a subsequent reverse learning test, which consisted in learning to exit the labyrinth from the opposite direction to that previously learned within a defined number of trials.

After 4 months of homotaurine supplementation, initial learning test was repeated, with the same modalities of the initial test.

The first evaluable results regarding the comparison between the cognitive learning tests, carried out on two groups of dogs over 10 years of age, a period in which aging-correlated brain behavior changes can be observed.

Figure 2:
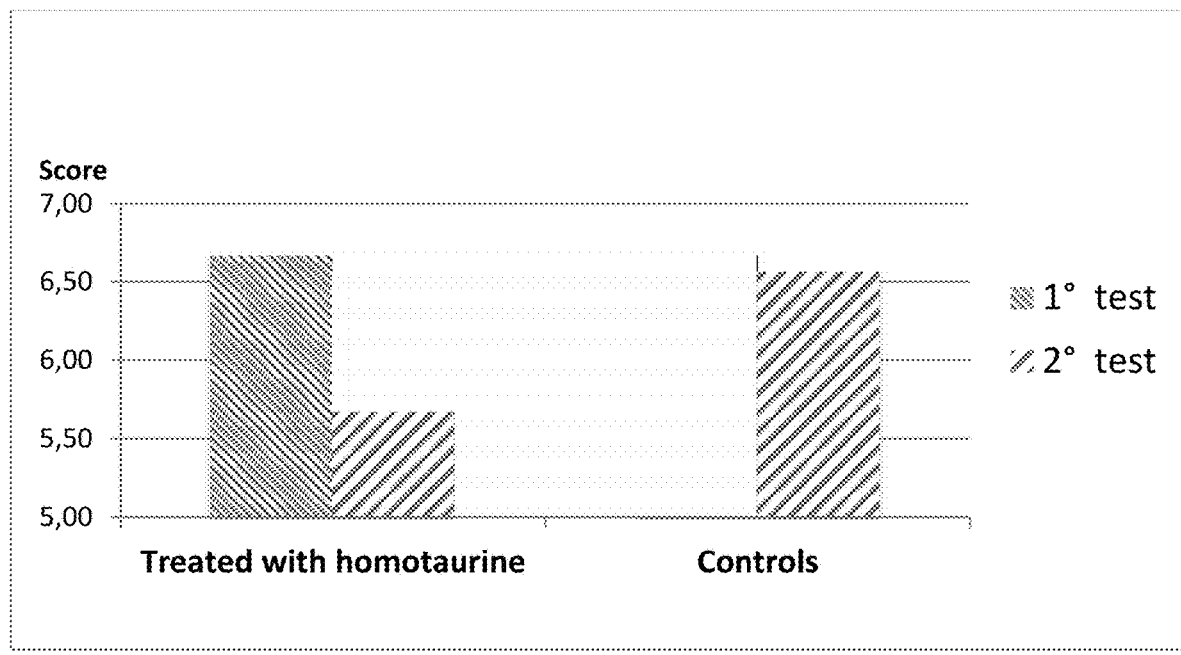
FIG. 2 is a graph showing the average number of wrong tries in the learning test of aged dogs who received a composition according to one embodiment of the present disclosure.

Results of the first test showed that twelve dogs homotaurine-implemented passed the test, and four dogs failed (25% of failures), with an average score (determined as the number of attempts necessary) of 6.67, while in the control group of eleven dogs passed the test and four dogs failed (27% of failures), with an average score of 6.36 (FIGS. 1 and 2 and Tables 1 and 2).

TABLE 1

Percentage of the aged dogs able to pass the learning test

|  | Treated with homotaurine | Controls |
|---|---|---|
| 1° test | 75% | 73% |
| 2° test | 75% | 60% |

TABLE 2

Average number of wrong tries of the aged dogs able to pass the learning test

|  | Treated with homotaurine | Controls |
|---|---|---|
| 1° test | 6.67 | 6.36 |
| 2° test | 5.67 | 6.56 |

The two groups gave substantially homogeneous results for the first test.

During the second test, conducted about four months later, homotaurine-implemented group gave the same results than before (25% of failures), but the average score decreased to 5.67 (−1.0) (FIGS. 1 and 2 and Tables 1 and 2).

In the control group, nine dogs passed the test while 6 failed (40% of failures, 13% more than in the first test). Moreover, their average score increased to 6.56 (+0.2).

In groups of young dogs (under 6 years of age) it was found a comparable trend, with a decrease in the average score in homotaurine-implemented group (−2.6) and an increase (+1.2) in the control group.

The data presented herein therefore suggests that a homotaurine-enriched diet in young non-human animals may contribute to delaying the onset of CDS and in maintaining mental wellness. The data presented herein also suggests that ingestion of homotaurine may improve mental condition and lessens ageing effect on the mental functioning of aged non-human animals.

Those skilled in the art will recognize, or be able to ascertain using no more than routine experimentation, numerous equivalents to the specific procedures, embodiments, claims, and examples described herein. Such equivalents are considered to be within the scope of this disclosure and covered by the claims appended hereto.

The contents of all references, issued patents, and published patent applications cited throughout this application are hereby incorporated by reference.

What is claimed is:

1. A method for improving memory and/or learning in a non-human animal, the method comprising administering an effective amount of a homotaurine, a homotaurine-enriched composition, or a homotaurine-enriched supplement to a non-human animal in need thereof, wherein the effective amount of homotaurine is between about 500 mg/day and about 5 g/day.

2. The method as defined in claim 1, wherein the homotaurine is 3-amino-1-propanesulfonic acid, a salt thereof, a zwitterionic form thereof, a solvate thereof or an analog thereof.

3. The method as defined in claim 1, further comprising administering one or more of a monoamine oxidase inhibitor, L-deprenyl hydrochloride, phosphatidylserine, pyridoxine, S-adenosyl-L-methionine, apoaequorin, flavonoids, *Gingko biloba* extract, resveratrol and d-alpha-tocopherol, botanical oils, medium-chain triglycerides, memantine, amantadine, adranafil, modafinil, vitamin E, vitamin A, Senilife, Neutricks, coconut oil, Omega-3 fatty acids, Propentofylline, Canine b/d, antioxidants, DL-alpha-lipoic acid, L-carnitine, botanic oils, Activait®, a-lipoic acid, carnitine, glutathione, and S-adenosyl-L-methionine.

4. The method as defined in claim 1, wherein the non-human animal is a canine.

5. The method as defined in claim 4, wherein the canine is a dog.

6. The method as defined in claim 1, wherein the non-human animal is an aged non-human animal.

7. The method as defined in claim 1, wherein the non-human animal is a young non-human animal.

8. The method as defined in claim 1, wherein the homotaurine-enriched composition comprises:
 i) homotaurine; and
 ii) one or more edible materials.

9. The method as defined in claim 8, wherein the homotaurine is 3-amino-1-propanesulfonic acid, a salt thereof, a zwitterionic form thereof, a solvate thereof or an analog thereof.

10. The method as defined in claim 8, wherein the homotaurine-enriched composition is for oral administration.

11. The method as defined in claim 8, wherein the homotaurine-enriched composition is food for the non-human animal.

12. The method as defined in claim 8, wherein the one or more edible materials is one or more of a protein source, a carbohydrate source, a fat source, a vegetable source, a vitamin source and a balancing agent.

13. The method as defined in claim 8, wherein the homotaurine-enriched composition is a nutritionally complete diet for the non-human animal.

14. The method as defined in claim 8, wherein the homotaurine-enriched composition is a nutritionally complete diet for an aged non-human animal.

15. The method as defined in claim 1, wherein the homotaurine-enriched supplement comprises an effective amount of a homotaurine or the homotaurine-enriched composition of claim 8 and at least one nutraceutically acceptable vehicle.

16. The method as defined in claim 15, wherein the homotaurine is 3-amino-1-propanesulfonic acid, a salt thereof, a zwitterionic form thereof, a solvate thereof or an analog thereof.

17. The method as defined in claim 15, wherein the homotaurine-enriched supplement is for oral administration.

18. The method as defined in claim 15, wherein the homotaurine-enriched supplement is for use as a supplement to the non-human animal diet.

* * * * *